(12) United States Patent
De Wael et al.

(10) Patent No.: US 12,372,491 B2
(45) Date of Patent: Jul. 29, 2025

(54) INTERPRETING AN ELECTROCHEMICAL RESPONSE

(71) Applicant: UNIVERSITEIT ANTWERPEN, Antwerp (BE)

(72) Inventors: Karolien De Wael, Sint-Pauwels (BE); Pierre Van Espen, Antwerp (BE); Robin Van Echelpoel, Brecht (BE); Mats De Jong, Geel (BE)

(73) Assignee: UNIVERSITEIT ANTWERPEN, Antwerp (BE)

(*) Notice: Subject to any disclaimer, the term of this patent is extended or adjusted under 35 U.S.C. 154(b) by 412 days.

(21) Appl. No.: 18/011,024

(22) PCT Filed: Jun. 18, 2021

(86) PCT No.: PCT/EP2021/066563
§ 371 (c)(1),
(2) Date: Dec. 16, 2022

(87) PCT Pub. No.: WO2021/255230
PCT Pub. Date: Dec. 23, 2021

(65) Prior Publication Data
US 2023/0236145 A1    Jul. 27, 2023

(30) Foreign Application Priority Data

Jun. 19, 2020 (EP) .................................. 20181041
Dec. 18, 2020 (EP) .................................. 20215395

(51) Int. Cl.
*G01N 27/327*    (2006.01)
*G01N 27/48*     (2006.01)
(Continued)

(52) U.S. Cl.
CPC ..... *G01N 27/3274* (2013.01); *G01N 27/3272* (2013.01); *G01N 27/3273* (2013.01);
(Continued)

(58) Field of Classification Search
CPC ............. G01N 27/327; G01N 27/3274; G01N 27/3272; G01N 27/3273; G01N 27/48;
(Continued)

(56) References Cited

FOREIGN PATENT DOCUMENTS

| WO | 2014070801 A1 | 5/2014 |
| WO | 2019076829 A1 | 4/2019 |

OTHER PUBLICATIONS

Borman et al., "Automated Algorithm for Detection of Transient Adenosine Release", ACS Chemical Neuroscience, vol. 8, No. 2, Feb. 15, 2017, pp. 386-393.
(Continued)

*Primary Examiner* — Gurpreet Kaur
(74) *Attorney, Agent, or Firm* — Workman Nydegger

(57) ABSTRACT

A computer-implemented method for interpreting an electrochemical response, comprises the steps of: (a) providing an electrochemical response that is baseline-corrected; (b) identifying in the electrochemical response one or more peaks that exceed a predetermined height threshold and a predetermined prominence threshold, each identified peak having a peak position; (c) providing a predetermined peak position range for each of a plurality of analytes; and (d) attributing one or more of the analytes to the peaks identified in step b, by, for each peak, associating the peak with an analyte when the peak position falls within the predetermined peak position range for the analyte.

15 Claims, 7 Drawing Sheets

(51) Int. Cl.
  *G01N 33/15*    (2006.01)
  *G01N 33/22*    (2006.01)
  *G01N 33/487*   (2006.01)
(52) U.S. Cl.
  CPC ............. *G01N 27/48* (2013.01); *G01N 33/15* (2013.01); *G01N 33/227* (2013.01); *G01N 33/48714* (2013.01)
(58) Field of Classification Search
  CPC ........ G01N 27/30; G01N 33/15; G01N 33/22; G01N 33/487; G03G 15/16; G03G 15/23; G03G 21/14
  See application file for complete search history.

(56)         References Cited

OTHER PUBLICATIONS

Van Echelpoel et al., "Unlocking the Full Potential of Voltammetric Data Analysis: A Novel Peak Recognition Approach for (Bio)analytical Applications", Talanta, vol. 233, Jun. 11, 2021, Elsevier, Amsterdam, NL, 7 pages.
Van Espen, Piet, "Spectrum Evaluation", Chapter 4, Handbook of X-ray Spectrometry, Second Edition, as early as Jan. 1, 2001, pp. 239-339.
Extended European Search Report from corresponding European Patent Application No. EP 20181041.3, Aug. 13, 2020.
International Search Report from corresponding PCT Application No. PCT/EP2021/066563, Aug. 30, 2021.

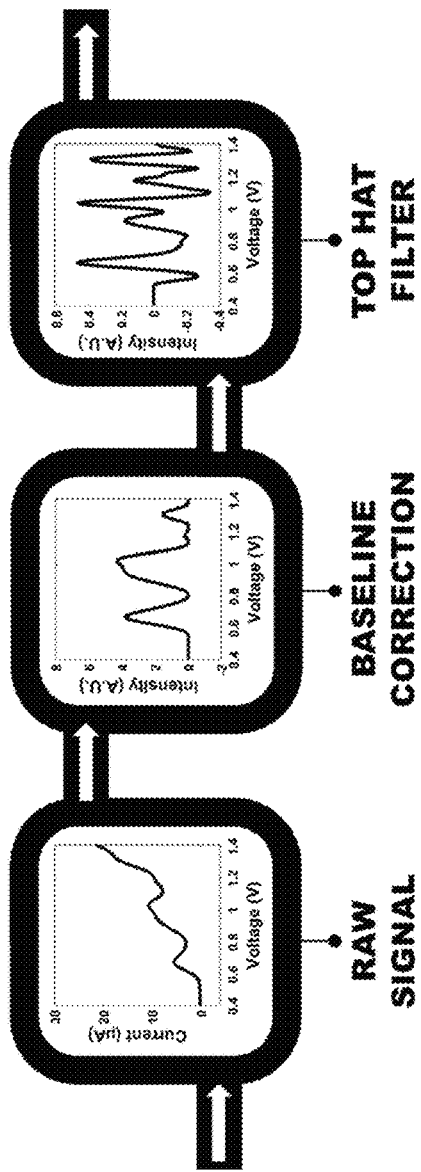
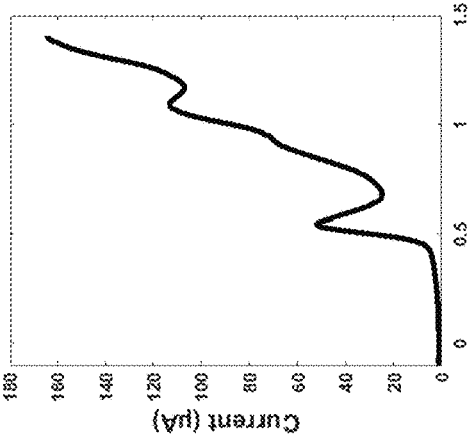
FIG 17
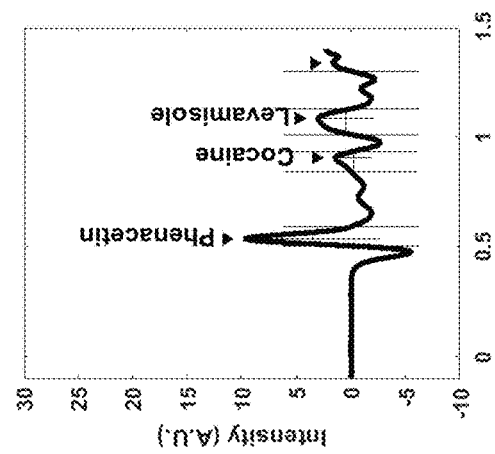
FIG 18
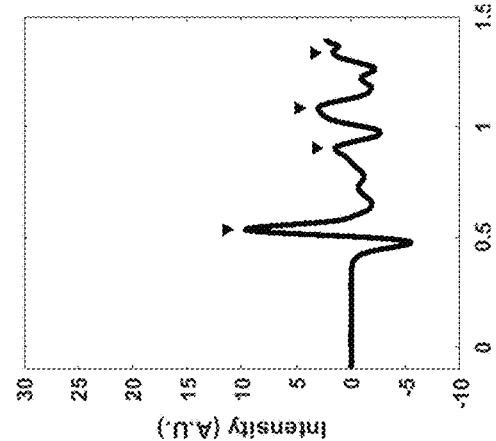
FIG 19
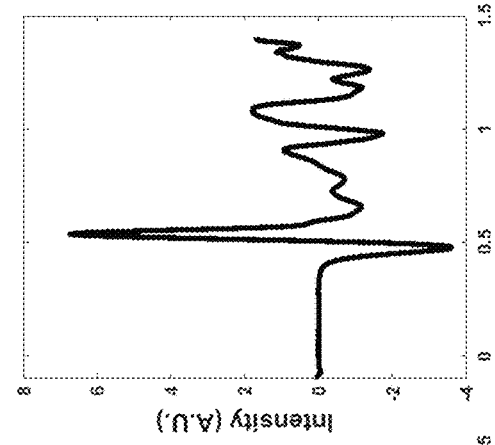
FIG 20
FIG 21
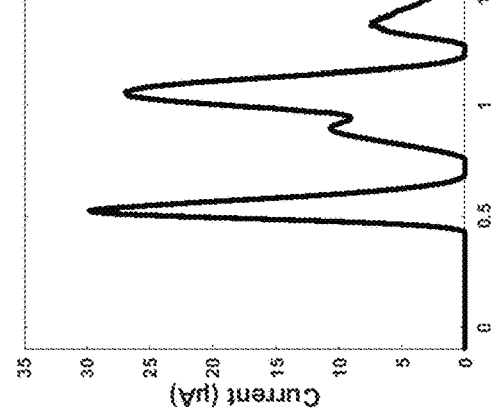
FIG 22

INTERPRETING AN ELECTROCHEMICAL RESPONSE

TECHNICAL FIELD OF THE INVENTION

The present invention relates to the interpretation of electrochemical responses and more in particular to the computer-implemented attribution of analytes to electrochemical peaks.

BACKGROUND OF THE INVENTION

Various analytical techniques are known in the art for analysing the contents of a sample, including techniques based on spectroscopy (e.g. UV/vis-, IR, fluorescence or Raman spectroscopy), microscopy (e.g. optical, X-ray or electron microscopy), electroanalysis (e.g. potentiometry or voltammetry), spectrometry (e.g. mass, ion-mobility or Rutherford backscattering spectrometry), calorimetry (e.g. differential scanning calorimetry), titrimetry (e.g. acid-base, redox titration or complexometric titration), chromatography (e.g. gas or liquid chromatography), gravimetric analysis and radioanalysis. For an arbitrary sample, one or more (e.g. a combination of) suitable techniques can generally be found by which one can fairly accurately determine the presence of one or more analytes, or—by extension—elucidate the entire chemical and/or elemental composition of the sample.

However, these techniques typically require bulky equipment, highly trained staff, involved procedures, specific materials (e.g. reagents), etc. They are therefore often only performed in specialized facilities, such as toxicological or forensic laboratories, research institutes or universities. These factors all add to the overall costs—especially in terms of time—needed to analyse a sample using these analytical techniques. Thus, although the information they provide would be highly beneficial to various personnel in the field—such as police officers, customs officers, anti-doping agents, environmental workers, etc.—so as to quickly make informed decisions, such information is most often not or only sparingly available to them at the time of need.

In seeking to remedy this, solutions in the form of portable analytical equipment (e.g. testers or testing kits) have been sought for some of the analytical techniques which do in principle lend themselves to being miniaturized. For example, a convenient system for performing electroanalysis can be realized by using electrodes with a small form factor—such as screen-printed electrodes—in combination with a portable (e.g. handheld) control-and-readout device. However, the output signal of an electrochemical measurement—i.e. the electrochemical response (e.g. a voltammogram)—is typically fairly complicated and considerable expertise is needed to correctly interpret it, particularly when the sample is a complex mixture of compounds. Moreover, the situation in the field may often demand swift results under stressful circumstances, which can hamper even the ability of experts to promptly draw accurate conclusions. As such, even if portable electroanalytical equipment is available, it remains largely impractical and inaccessible to the general person in the field.

In the context of e.g. outlining a subject's complicity in a firearm-related crime in a simpler manner, WO2014070801A1 describes the identification of a chemical agent—such as gunshot residue or explosive residue—and determination of the level of exposure using electrochemical detection and advanced signal processing. The disclosed examples include sampling for gunshot residue, examining the electroanalytical fingerprint of the sample using cyclic square-wave voltammetry, processing the resulting data with Fast Fourier Transform (FFT) and performing pattern-recognition—using a Discriminant Function Analysis (DFA) treatment—to classify the data among pre-selected data sets. The classification can be used to discriminate between no exposure to gunshot residue, secondary exposure from surfaces and air, exposure from loading a firearm, and primary exposure from the discharge of a firearm. As such, it could for example provide a much-needed forensic tool to implicate suspects and identify culpability in the field.

However, even though WO2014070801A1 shows a method for relatively easily judging a subject's complicity in a firearm-related crime, it does not provide for a way to identify individual analytes (e.g. gunshot residue components). This may be less of an issue for gunshot residue or explosive residue, but the ability to discern individual analytes may be highly desired in other contexts—for example, when analysing samples suspected to contain illicit drugs, performance enhancing drugs or antibiotics. Moreover, the described method is not necessarily straightforwardly transferable to such different contexts. As such, there is thus still a need in the art for ways to interpret an electrochemical response which addresses at least some of the challenges outlined above.

Borman et al. (BORMAN, Ryan P., et al. Automated algorithm for detection of transient adenosine release. *ACS chemical neuroscience*, 2017, 8.2: 386-393.) noted that spontaneous adenosine release events have been discovered in the brain that last only a few seconds, and that the identification of these adenosine events from fast-scan cyclic voltammetry (FSCV) data is difficult due to the random nature of adenosine release. In this context, they developed an algorithm that automatically identifies and characterizes adenosine transient features from a three dimensional colour plot (i.e. the FSCV data plotted as current in function of both voltage and time). More concretely, the algorithm identifies adenosine based on its two oxidation peaks, the time delay between them, and their current vs. time peak ratios. Accordingly, the algorithm of Borman et al. is specifically configured to identify one analyte (adenosine), not a plurality of different analytes simultaneously.

SUMMARY OF THE INVENTION

It is an object of the present invention to provide a good computer-implemented method for interpreting an electrochemical response. It is a further object of the present invention to provide a good computer-implemented method for detecting one or more analytes in a sample based on the aforementioned method. It is a yet further object of the present invention to provide a good data processing system, computer program and computer-readable medium associated with these methods. This objective is accomplished by methods, data processing systems, computer programs and computer-readable media according to the present invention.

It is an advantage of embodiments of the present invention that an electrochemical response can be quickly and accurately interpreted. It is a further advantage of embodiments of the present invention that the analytes in a sample can be quickly and accurately detected.

It is an advantage of embodiments of the present invention they are easily accessible for even untrained personnel. It is a further advantage of embodiments of the present invention they output results which can be readily understood—e.g. even by non-experts and under challenging circumstances—and which can allow various personnel to quickly make informed decisions.

It is an advantage of embodiments of the present invention they can be integrated in portable electroanalysis equipment or systems, which can be conveniently deployed and employed in the field.

It is an advantage of embodiments of the present invention they are time- and cost-effective.

It is an advantage of embodiments of the present invention that they are applicable—e.g. save for some adjustments in the parameters used—to a variety of electrochemical responses and electrochemical measurement techniques therefor.

It is an advantage of embodiments of the present invention that multiple analytes can be attributed simultaneously. It is a further advantage of embodiments of the present invention electrochemical response analytes from a variety of different classes (e.g. including drugs, adulterants, antibiotics and/or explosives) can be attributed.

It is an advantage of embodiments of the present invention that only those peaks which are prominent enough so that their peak position can be determined with sufficient accuracy are considered for attributing analytes thereto.

It is an advantage of embodiments of the present invention that the demarcation of peaks in the electrochemical response can be improved.

It is an advantage of embodiments of the present invention that a variety of exception rules (cf. infra) can be accounted for; e.g. where an analyte is known to have multiple detectable peaks but not all these peaks have been found in the electrochemical response, attribution of the analyte can be refused or revoked. It is a further advantage of embodiments of the present invention that exception rules can be implemented in an easy, straightforward and efficient manner.

In a first aspect, the present invention relates to a computer-implemented method for interpreting an electrochemical response, comprising the steps of: (a) providing an electrochemical response which is baseline-corrected; (b) identifying in the electrochemical response one or more peaks which exceed a predetermined height threshold and a predetermined prominence threshold, each identified peak having a peak position; (c) providing a predetermined peak position range for each of a plurality of analytes; and (d) attributing one or more of the analytes to the peaks identified in step b, by—for each peak—associating the peak with an analyte when the peak position falls within the predetermined peak position range for said analyte.

In a second aspect, the present invention relates to a computer-implemented method for detecting one or more analytes in a sample, comprising the steps of: providing an electrochemical response of the sample, and performing the method according to any embodiment of the first aspect using said electrochemical response of the sample.

In a third aspect, the present invention relates to a data processing system adapted to carry out the computer-implemented method according to any embodiment of the first or second aspect.

In a fourth aspect, the present invention relates to a computer program comprising instructions which, when the program is executed by a computer, cause the computer to carry out the computer-implemented method according to any embodiment of the first or second aspect.

In a fifth aspect, the present invention relates to a computer-readable medium comprising instructions which, when executed by a computer, cause the computer to carry out the computer-implemented method according to any embodiment of the first or second aspect.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

additional rules, to extent the scope, can be integrated in the software by means of an exception module that is placed right before the peak assignment. FIG. 15 shows how an additional rule can be incorporated that requires the presence of both peaks of ketamine ahead of assignment. Another possibility would be a rule where two compounds can never be assigned together (FIG. 16).

FIG. 17 schematically depicts the preprocessing steps in accordance with illustrative embodiments of the present invention.

FIG. 18-FIG. 22 schematically depicts the different steps of the algorithm in accordance with illustrative embodiments of the present invention, applied to the cocaine sample case study (cf. supra): raw voltammogram (FIG. 18), baseline correction (FIG. 19), application of the top hat filter (FIG. 20), peak identification (FIG. 21) and compound assignment (FIG. 22).

Figure 1:
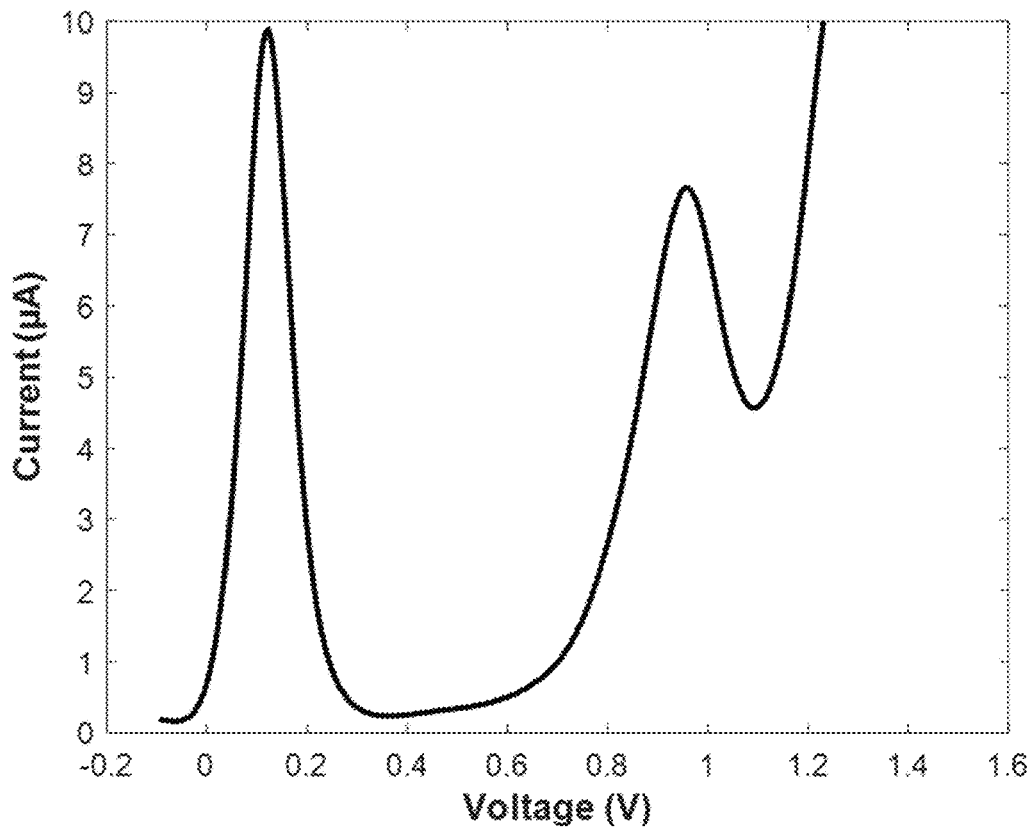
FIG. 1 shows a raw voltammogram in accordance with illustrative embodiments of the present invention.

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable with their antonyms under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. The term "comprising" therefore covers the situation where only the stated features are present and the situation where these features and one or more other features are present. Thus, the scope of the expression "a device comprising means A and B" should not be interpreted as being limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practised without these specific details. In other instances, well-known methods, structures and techniques have not been shown in detail in order not to obscure an understanding of this description.

The following terms are provided solely to aid in the understanding of the invention.

As used herein, and unless otherwise specified, an 'electrochemical response' is a signal from an electrochemical measurement (e.g. from an electroanalysis).

As used herein, and unless otherwise specified, 'applying a filter' or 'filtering' is a form of signal processing which aims to at least partially (e.g. completely) suppress an unwanted aspect (e.g. a component or feature) of the signal.

In a first aspect, the present invention relates to a computer-implemented method for interpreting an electrochemical response, comprising the steps of: (a) providing an electrochemical response which is baseline-corrected; (b) identifying in the electrochemical response one or more peaks which exceed a predetermined height threshold and a predetermined prominence threshold, each identified peak having a peak position; (c) providing a predetermined peak position range for each of a plurality of analytes; and (d) attributing one or more of the analytes to the peaks identified in step b, by—for each peak—associating the peak with an analyte when the peak position falls within the predetermined peak position range for said analyte.

Whereas the prior art (e.g. WO2014070801A1) focusses on pattern-recognition to interpret the electrochemical response—thus seeking to match the electrochemical response as a whole with pre-selected data sets—, the present invention is instead based on peak-recognition—i.e. identifying and subsequently attributing individual peaks. The latter is advantageously more flexible, particularly with respect to identify individual analytes in a (potential complex) mixture of compounds. Indeed, the present approach advantageously allows to detect analytes of interest in relatively arbitrary mixtures of varying concentrations, even in the presence of unknown analytes (e.g. analytes for which no predetermined peak position range is known). By contrast, pattern-recognition would generally require data on each potential mixture individually, as even changes in concentration of analytes may quickly yield a completely different pattern and thereby throw off the algorithm. This is only feasible in specific contexts (e.g. detection of gun powder residue)—where the variations in sample composition are relatively limited—but quickly becomes unwieldy when the sample variation increases—such as in the context of illicit drug searches, where samples with relatively arbitrary mixtures of illicit drugs and various adulterants are commonplace.

The invention is in general not limited by the nature of the electrochemical response (e.g. whether the signal takes the form of 'current vs potential' or some other appropriate quantities) or the technique used for acquiring it. The aforementioned notwithstanding, the electrochemical response may in preferred embodiments correspond to a relationship between current and potential (or quantities derived therefrom); for example, the electrochemical response may be a voltammogram. In embodiments, the electrochemical response may typically be a two-dimensional response—such as a measured output (e.g. current) in function of an input (e.g. potential), or quantities derived therefrom—; rather than e.g. a three-dimensional dimensional response—i.e. such as a measured output (e.g. current) in function of two inputs (e.g. potential and time), or quantities derived therefrom. In embodiments, the electrochemical response may have been acquired using a voltammetric technique or an amperometric technique, preferably a voltammetric technique. In preferred embodiments, the voltammetric technique may be a square-wave voltammetry. Square-wave voltammetry is typically a very sensitive electrochemical measurement technique, thereby advantageously yielding electrochemical responses which can then be interpreted with good accuracy. In some embodiments, the electrochemical measurement technique may comprise a cathodic and/or anodic pretreatment before acquiring the electrochemical response.

In embodiments, step a may comprise: (a1) providing an electrochemical response, and (a2) performing a baseline-correction on the electrochemical response. In embodiments, the electrochemical response may be baseline-corrected using a moving average baseline-correction. In other embodiments, the electrochemical response may be baseline-corrected by filtering the electrochemical response (cf. infra).

In embodiments, the method may further comprise a step a'—before step b—of: (a') applying a filter to the electrochemical response so as to improve peak demarcation. In embodiments, the filter may be a zero-area filter, preferably a zero-area rectangular filter. In embodiments, the zero-area rectangular filter may be a top-hat filter, a square-wave filter or a symmetric square-wave filter, preferably a top-hat filter. These filters have been previously described by Van Espen (VAN ESPEN, Piet. Spectrum evaluation. *Handbook of X-ray Spectrometry*, 2002, 4: 239-339.), which is incorporated herein by reference. Convoluting—in a form of correlation technique—the electrochemical response with a filter that approximates the shape of the peaks, advantageously yields a transformed electrochemical response in which the peaks are advantageously emphasized. In doing so, the peak demarcation is improved—for example, because overlapping peaks are (partially) resolving (e.g. peaks which appear as shoulders become separated from the main peak)—and the individual peaks become more readily locatable. Moreover, when the filter is a zero-area filter, the background (i.e. continuum) is at the same time effectively (further) suppressed. The simplest and most effective filters belong to the group of zero-area rectangular filters; such as a zero-area top-hat filter, zero-area triangular filter or zero-area gaussian filter. These filters posses a net zero area and typically have a central window with positive coefficients and two side lobes with negative coefficients. An important and preferred e.g. because it can be easily implemented and requires minimal computing time (even compared to e.g. a zero-area gaussian filter)—representative of this group of filters is the top-hat filter, which has a central window with an odd number of channels w and constant positive coefficients, and two side windows each v channels wide and with constant negative coefficients. The value of the filter coefficients follows from the zero-area constraint:

$$h_k = \begin{cases} -\frac{1}{2v}, & -v-\frac{w}{2} \le k < -\frac{w}{2} \\ \frac{1}{w}, & -\frac{w}{2} \le k \le +\frac{w}{2} \\ -\frac{1}{2v}, & +\frac{w}{2} < k \le \frac{w}{2}+v \end{cases}.$$

The filtered (i.e. transformed) electrochemical response is then obtained by the convolution of the electrochemical response with the filter:

$$y_i^* = \sum_{k=-v-w/2}^{v+w/2} h_k y_{i+k}.$$

It will be clear that w and v may in embodiments be selected in function of the particulars of the electrochemical response that is being processed. Suitable values can typically at least be found by trial-and-error. The aforementioned notwithstanding, w may in embodiments be in the range of from 3 to 11, preferably from 5 to 9, such as 7. In embodiments, v may be equal to the floor of w/2 ($\lfloor w/2 \rfloor$ or floor(w)). Other zero-area rectangular filters may also be used, such as the square-wave filter with typical coefficient sequence −1, −1, 2, 2, −1, −1 or the symmetric square-wave filter with coefficients −1, 1, 1, −1.

In embodiments, step a' may be performed after or concurrently with step a. In some embodiments, step a may comprise providing an electrochemical response which is baseline-corrected and filtered. In embodiments, step a' may be performed after or concurrently with step a2. Since filtering with a zero-area filter can at the same time effectively suppress the background, it may in embodiments be sufficient to directly filter an uncorrected (e.g. raw) electrochemical response; as opposed to first baseline-correcting the electrochemical response and then subsequently filtering it.

The prominence of a (signal) peak is a measure for how much the peak stands out due to its intrinsic peak height and its peak location relative to other peaks; it is akin to the concept of prominence in topography. A low isolated peak can be more prominent than one that is higher but is an otherwise unremarkable member of a tall range. In the context of interpreting an electrochemical response, less prominent peaks are those which largely overlap with other peaks and/or which do not stick out considerably from the background signal. Since these peaks are thus mostly engulfed by the surrounding peaks and/or the background signal, they tend to be more ill-defined, so that there is less certainty on their exact position. Thus, by employing a prominence threshold, it is advantageously ensured that only those peaks are considered for which the peak position can be determined with sufficient accuracy. The prominence of a peak can be established as follows: (1) extend a horizontal line from the peak maximum to the left and right until the line either: crosses the signal because there is a higher peak, or reaches the left or right end of the signal; (2) find the minimum of the signal in each of the two intervals (i.e. left and right of the peak maximum) defined in step 1, this point is either a valley or one of the signal endpoints; (3) the higher of the two interval minima specifies a reference level, the peak prominence is the height of the peak above this reference level.

It will be clear that an appropriate predetermined height threshold and predetermined prominence threshold will typically depend on the particulars of the electrochemical response that is being processed. For example, these values may change considerably depending on whether the electrochemical response is filtered or not, and even what type of filter is used. Suitable values can typically at least be found by trial-and-error. To nevertheless give some general guidance: for baseline corrected electrochemical responses which were filtered using a top-hat filter with w=7 and v=⌊w/2⌋, it was found suitable to select the predetermined height threshold in the range of −0.60 to −0.20, preferably −0.40. Under the same conditions, it was found suitable to select the predetermined prominence threshold in the range of 0.10 to 0.40, preferably 0.25. Note that in this context, a predetermined height (or prominence) threshold is considered 'exceeded' by a peak height (or prominence) larger than or equal to the threshold. As such, if one were to interpret 'exceed' as strictly 'larger than', then the mentioned values should be adjusted accordingly.

In some embodiments, the peak position may be the position (e.g. 'x-value') corresponding to the peak maximum (i.e. maximum height/intensity/'y-value' for the peak). In other embodiments, a curve may be fitted to the peak and the peak position may be determined from the maximum of that curve; rather than from the peak maximum as such.

Step c comprises providing at least one predetermined peak position range for each of the plurality of analytes. However, where the analyte is known to have multiple detectable peaks (e.g. detectable under the applicable measurement conditions), a predetermined peak position range can be provided for each of the detectable analyte peaks. The predetermined peak position ranges are generally independently selected for each analyte (and each analyte peak); e.g. based on previously observed peak positions for the corresponding analyte (or analyte peak). Note that this includes also independently selecting the width of the range; e.g. in function of the variation that is observed for a particular analyte (or analyte peak). In embodiments, the predetermined peak position ranges may depend on the measurement conditions used when recording the electrochemical response. For example, different ranges may be used depending on the measurement pH. As such, the predetermined peak position ranges may preferably be selected based on previously observed peak positions for the corresponding analyte (or analyte peak) under the same—or equivalent—measurement conditions. In embodiments, a predetermined peak position range may be expressed as a range between minimum and maximum peak position, or as an average peak position in combination with a variance factor.

In embodiments, step d may comprise—for each peak— iterating over all the analytes and associating the peak with each analyte for which the peak position falls within the predetermined peak position range for said analyte. Since the predetermined peak position ranges for different analytes (or analyte peaks) may overlap, it is possible that multiple analytes (or analyte peaks) are attributed to a single peak. Nevertheless, an easier and more straightforward implementation is advantageously achieved by first provisionally associating the possible analytes (or analyte peaks) to a peak and then—where applicable—altering the association based on one or more predetermined exception rules (cf. infra).

In embodiments, step d may further comprise altering the association of a peak with one or more of the analytes based on a predetermined exception rule. This advantageously allows to reduce—where possible—the number of multiple associations. In some embodiments, altering the association of the peak with one or more of the analytes may comprise disassociating (i.e. revoking the attribution of) the peak from one or more of the analytes. In other—alternative or complementary—embodiments, altering the association of the peak with one or more of the analytes may comprise associating the peak with one or more of the analytes. Several different predetermined exception rules can be envisioned; these may include priority rules (i.e. when a predetermined condition is met, one or more analytes take precedence over one or more other analytes and thus the latter should be disassociated from the peak if the former have been associated), exclusion rules (i.e. when a predetermined condition is met, one or more analytes should be refused and thus disassociated from the peak), modification rules (i.e. when a predetermined condition is met, alternative predetermined peak position ranges should be used for one or more analytes and the association should be altered accordingly) or operation rules (i.e. when a predetermined condition is met, a modification to the steps of the method should be done). In embodiments, a predetermined exception rule may (conceptually) comprise a logic gate, such as an OR-, AND-, NOR-, NAND- or XOR-gate. Examples of priority rules could be: (i) where an analyte should take precedence over another analyte, prioritize the former over the latter; (ii) where an analyte is known to have multiple detectable peaks and all these analyte peaks have been associated with the peaks that were identified (i.e. all the analyte peaks were found in the electrochemical response), prioritize this analyte (i.e. these analyte peaks) over analytes with only a single detectable peak (or over analytes with less detectable peaks); and/or (iii) where one or more analytes are known to frequently occur together and all these analyte peaks have been associated with the peaks that were identified, prioritize these analytes over other analytes. An example of an exclusion rule could be: (iv) where an analyte is known to have multiple detectable peaks but not all these analyte peaks have been associated with the peaks that were identified (i.e. not all the analyte peaks have been found in the electrochemical response), refuse the analyte; and/or (v) where an analyte peak from a first analyte is known not to occur together with a second analyte (e.g. because the latter shifts the analyte peak of the first analyte), refuse association of (e.g. disassociate) the analyte peak with the first analyte. An example of a modification rule could be: (vi) where the presence of an analyte is known to shift the peak of one or more other analytes and the former has been associated, use alternative predetermined peak position ranges for the latter and alter the association accordingly. An example of an operation rule could be: (vii) when a certain peak is detected, stop step d (and e.g. go immediately to step e). It will be clear that these rules may also be further finetuned; for example, rule ii may take into account the relative height of the multiple detectable peaks and the priority may only be applied if the peaks that were identified match conform with this relative height. In embodiments, step d may comprise the use of one or more of the aforementioned rules.

In embodiments, step d may further comprise attributing peaks to which no analyte is associated (e.g. to which no analyte is any longer associated) to an unknown analyte.

In embodiments, the method may further comprise a step e—after step d—of: (e) outputting the attributed analytes. In embodiments, step e may comprise outputting a list of the attributed analytes and/or a graph annotated with the attributed analytes.

In embodiments, the plurality of analytes may comprise one or more from the list of drugs—such as psychoactive drugs (e.g. illicit drugs, such as narcotics), pharmaceutical drugs (e.g. medicaments) or performance enhancing drugs (e.g. doping)—, adulterants (e.g. cutting agents), antibiotics and explosives (e.g. gun powder, a chemical explosive, gun powder residue or explosive residue).

In embodiments, any feature of any embodiment of the first aspect may independently be as correspondingly described for any embodiment of any of the other aspects.

In a second aspect, the present invention relates to a computer-implemented method for detecting one or more analytes in a sample, comprising the steps of: providing an electrochemical response of the sample, and performing the method according to any embodiment of the first aspect using said electrochemical response of the sample.

The invention is in general not limited by the nature of the sample (e.g. whether the sample is in the gas, liquid or solid phase) or the way in which it was sampled. The aforementioned notwithstanding, the sample may be dissolved in an aqueous environment, such as a buffer (e.g. a phosphate-buffered saline, PBS). In embodiments, a pH of the solution may be from 0 to 14, preferably from 3 to 14, yet more preferably from 5 to 14, still more preferably from 6 to 13, most preferably from 7 to 12, such as 7 or 12.

In embodiments, providing an electrochemical response of the sample may comprise performing an electrochemical measurement on a solution may comprise the sample.

In embodiments, any feature of any embodiment of the second aspect may independently be as correspondingly described for any embodiment of any of the other aspects.

In a third aspect, the present invention relates to a data processing system adapted to carry out the computer-implemented method according to any embodiment of the first or second aspect.

In some embodiments, the data processing system may be a generic data processing system (e.g. a personal computer, laptop or smartphone). In other—alternative or complementary— embodiments, the data processing system may be part of an analytical equipment (e.g. a tester or testing kit), such as an analytical apparatus. In embodiments, the analytical equipment may be a portable analytical equipment (e.g. a portable analytical apparatus). The analytical equipment may for example further comprise electrodes and a source for performing an electrochemical measurement. In some case, the analytical equipment may also further comprise a sample holder and/or a measurement phase (e.g. a buffer) for performing the electrochemical measurement.

In embodiments, any feature of any embodiment of the third aspect may independently be as correspondingly described for any embodiment of any of the other aspects.

In a fourth aspect, the present invention relates to a computer program comprising instructions which, when the program is executed by a computer, cause the computer to carry out the computer-implemented method according to any embodiment of the first or second aspect.

In embodiments, an input for the computer program may be a baseline-corrected electrochemical response. In alternative embodiments, the input for the computer program may be an uncorrected (e.g. raw) electrochemical response. Thus, the electrochemical response may be corrected outside the computer program or by the computer program as such.

In embodiments, an input for the computer program may be a filtered electrochemical response (e.g. a filtered baseline-corrected electrochemical response). In alternative embodiments, the input for the computer program may be an unfiltered electrochemical response. Thus, the electrochemical response may be filtered outside the computer program or by the computer program as such.

In some embodiments, the predetermined peak position ranges may be coded into the computer program. In other embodiments, the predetermined peak position ranges may be retrieved from a database.

In embodiments, the computer program may be adapted for selecting (e.g. automatically or based on user input) the analytes which are to be used. For example, the computer program may comprise different modules—each corresponding to a selection of analytes—and a user may select the module to be used.

In embodiments, the computer program may be adapted for performing an electrochemical measurement and acquiring an electrochemical response therefrom. In such instances, the computer program may typically be executed by a computer (e.g. a data processing system) which is part of an analytical equipment (cf. supra). Such a computer program advantageously allows to directly combine the measurement of a sample and the interpretation of the corresponding results, thus greatly facilitating the overall act for a user.

In embodiments, the computer program may be adapted for controlling the measurement conditions (e.g. a pH, and/or whether or not a cathodic and/or anodic pretreatment is performed) prior to or as part of the electrochemical measurement. Depending on the analytes to be detected, some measurement conditions can advantageously allow to improve the detection of an analyte and/or the interpretation of the electrochemical response (e.g. by shifting the peaks of some analytes, thereby for instance separating overlapping peaks). For example, where analytes are to be detected of which peaks are known to overlap under a first set of measurement conditions, but not under a second set of measurement conditions, the computer program may ensure that the second set is used. Controlling the measurement conditions may for instance be in the form a prompt requesting a user action (e.g. adding a chemical to adjust the pH and/or starting a pretreatment), or the computer program may directly initiate the corresponding action(s). In some embodiments, the computer program may be adapted for performing a first electrochemical measurement at a first set of measurement conditions (e.g. without pretreatment and/or at a first pH) and a second electrochemical measurement at a second set of measurement conditions (e.g. with a pretreatment—such as a cathodic and/or anodic pretreatment—and/or at a second pH). In embodiments, the computer program may be adapted for interpreting the first electrochemical response (i.e. corresponding to the first electrochemical measurements) together with the second electrochemical response (i.e. corresponding to the second electrochemical measurements). For example, where analytes are to be detected of which peaks are known to overlap under a first—but not a second—set of measurement conditions, while other peaks are known to overlap under the second—but not the first—set of measurement conditions, electrochemical measurements may be performed for both and the computer program may e.g. detect the former peaks in the second electrochemical response and the latter in the first.

In embodiments, the computer program may be adapted for disabling (e.g. permanently) one ore more electrodes after having performed the electrochemical measurement. Disabling an electrode may for example be realized using an electrical pulse (e.g. a short circuit). By (permanently) disabling an electrode, it can be made unfit for re-use, thus promoting the use of new electrodes and thereby impeding cross-contamination (e.g. contamination of a new sample by an electrode with remains from a previous sample).

In embodiments, any feature of any embodiment of the fourth aspect may independently be as correspondingly described for any embodiment of any of the other aspects.

In a fifth aspect, the present invention relates to a computer-readable medium comprising instructions which, when executed by a computer, cause the computer to carry out the computer-implemented method according to any embodiment of the first or second aspect.

In embodiments, any feature of any embodiment of the fifth aspect may independently be as correspondingly described for any embodiment of any of the other aspects.

The invention will now be described by a detailed description of several embodiments of the invention. It is clear that other embodiments of the invention can be configured according to the knowledge of the person skilled in the art without departing from the true technical teaching of the invention, the invention being limited only by the terms of the appended claims.

Example 1

As a proof of concept, a computer program in accordance with the present invention was used to determine the presence in a sample of a number of analytes (e.g. illicit drugs and adulterants) which are known to frequently appear together. The analytes initially included ketamine, cocaine, paracetamol and silver, but this list could be easily extended with other relevant analytes (e.g. caffeine, creatine, mephedrone, methamphetamine, etc.).

Figure 2:
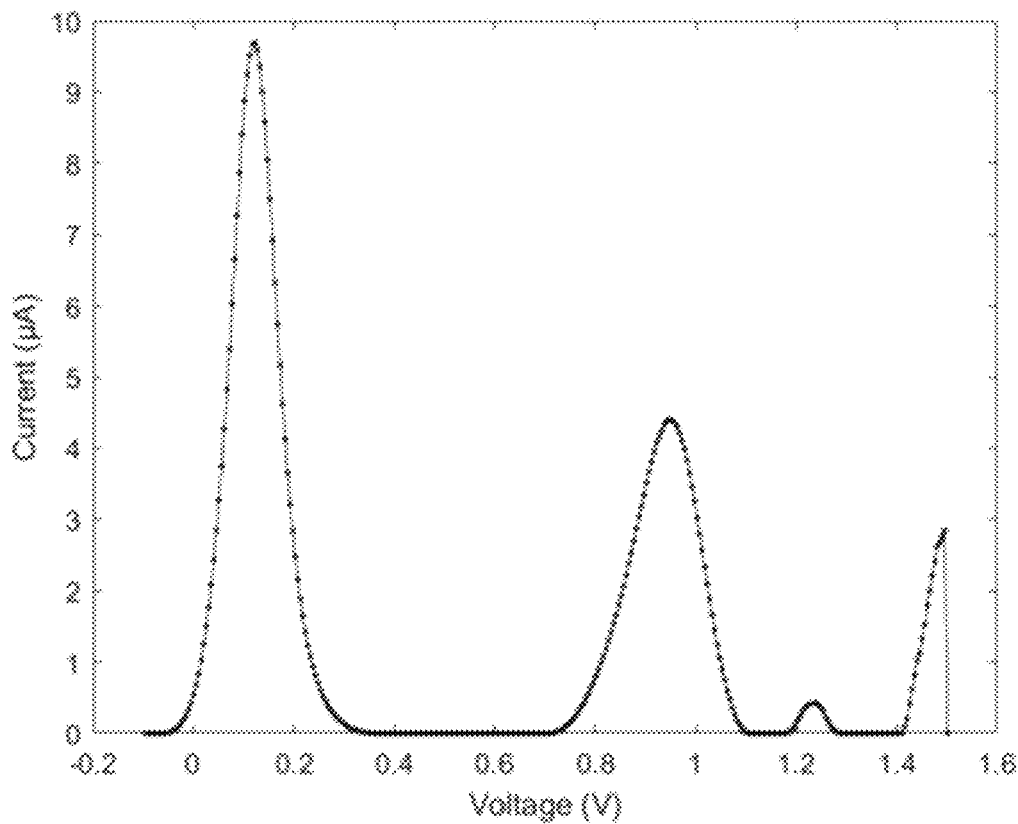
FIG. 2 shows a baseline-corrected voltammogram in accordance with illustrative embodiments of the present invention.

For the proof of concept, an electrochemical response of the sample was first obtained. In this example, the sample was dissolved in a pH 12 phosphate-buffered saline (PBS) buffer—which also functioned as a supporting electrolyte for the electrochemical measurement—and a square-wave voltammetry was performed thereon. The raw electrochemical response—shown in FIG. 1—was acquired using commercial software (PSTrace by PalmSens) and was subjected to a moving average baseline correction in the same software. The resulting baseline-corrected voltammogram is shown in FIG. 2. However, it will be clear that these specific details are only illustrative and that the present invention is not limited thereto. Indeed, a computer program in accordance with the present invention can generally be straightforwardly adapted to process (baseline-corrected) electrochemical responses acquired under different circumstances—such as different measurement conditions (e.g. different pH, different buffer, direct measurement of the solid sample instead of dissolved sample, cathodic and/or anodic pretreatment, etc.), different measurement techniques, different acquisition and/or correction software (e.g. built into the computer program itself), different type of baseline correction, etc.

Figure 3:
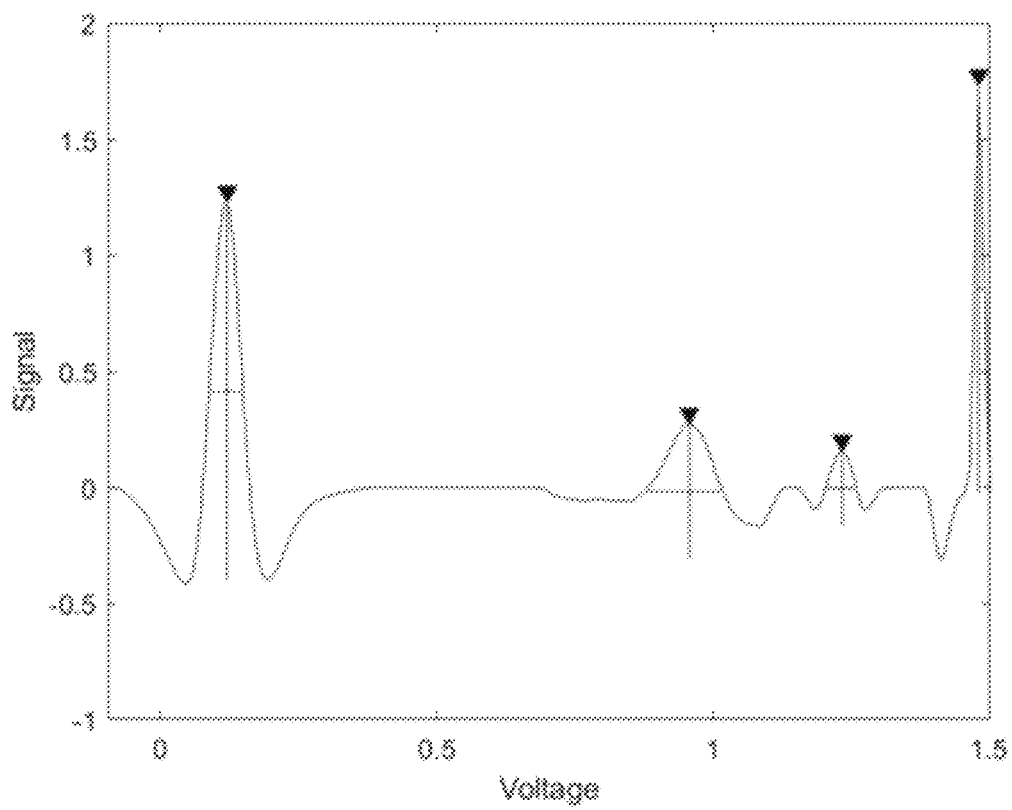
FIG. 3 shows a filtered electrochemical response in accordance with illustrative embodiments of the present invention.

The baseline-corrected voltammogram was input into the computer program and was filtered using a top-hat filter with $w=7$ and $v=\lfloor w/2 \rfloor$, thereby improving the peak separation. However, it will again be clear that other filters (e.g. another zero-area rectangular filter; cf. supra)—or even no filtering—can also be envisioned. The peaks in this filtered electrochemical response which exceeded a predetermined height threshold and a predetermined prominence threshold were then identified and their peak position (e.g. the position of their peak maximum) was determined. The outcome is visualized in FIG. 3, which shows the filtered electrochemical response with arrow heads indicating the peak maxima of those identified peaks which exceeded the predetermined height threshold (in this example, this corresponded to a peak height of −0.4 or more in the units as shown in FIG. 3) and predetermined prominence threshold (in this example, this corresponded to a peak prominence of 0.25 or more in the units as shown in FIG. 3), and a vertical line under each arrow head portraying the corresponding peak prominence. The horizontal line crossing each prominence line represents the 'full width at half prominence', though this parameter was not further used by the computer program. Note that although no units are explicitly indicated for the filtered signal (i.e. y-axis) in FIG. 3, these are not strictly arbitrary. Indeed, the values for the filtered signal are those which resulted directly from the filtering applied on the voltammogram of FIG. 2. Meanwhile the voltage (i.e. x-axis) in FIG. 3 remains in volts (V) as in FIG. 2, since the filtering used had no direct thereon.

Next one or more of analytes were attributed to the identified peaks. The computer program therefore comprised (or retrieved, e.g. from an associated database) at least one predetermined peak position range (e.g. defined by a e.g. minimum and maximum peak position) for each of the analytes for which the presence was to be determined. The predetermined peak position ranges can for example be selected based on previously observed peak positions for the corresponding analyte under the same—or equivalent—measurement conditions. Moreover, when the analyte is known to have multiple detectable peaks under these conditions, a predetermined peak position range can be used for each of the detectable peaks. In the present example, this was the case for ketamine, of which two peaks were known to be detectable. In order to interpret the peaks, the computer program then first iterated over all peaks, checking for each peak whether the peak position fell within the predetermined peak position range for an analyte (or analyte peak) and—if so—associating the peak with the analyte.

Since predetermined peak position ranges for different analytes (or analyte peaks) can in principle overlap, it is possible that multiple analytes (or analyte peaks) are hereby associated with a single peak. Moreover, the presence of one analyte may sometimes shift the peak of one or more other analytes, in which case alternative predetermined peak position ranges should be used for the latter. To reduce—where possible—the number of these occurrences, exception rules were further included into the computer program. Such an exception rule could for instance be that if—for an analyte of which it is known that multiple peaks should always be detectable (e.g. two peaks for ketamine)—some but not all those peaks were found in the electrochemical response, then none of these peaks should be associated with this analyte. Thus, after having provisionally associated the possible analytes (or analyte peaks) to a peak (or to each of the peaks), the computer program then subsequently applied the exclusion rules to—where needed—disassociate one or more peaks from one or more analytes. If—after having applied these exclusion rules—cases remain where multiple analytes (or analyte peaks) are associated to a single peak, these can be maintained and the output can reflect that the attribution was not fully conclusive.

Moreover, the computer program attributed peaks for which the peak position does not fall within any of the predetermined peak position ranges as belonging to an unknown analyte.

Figure 4:
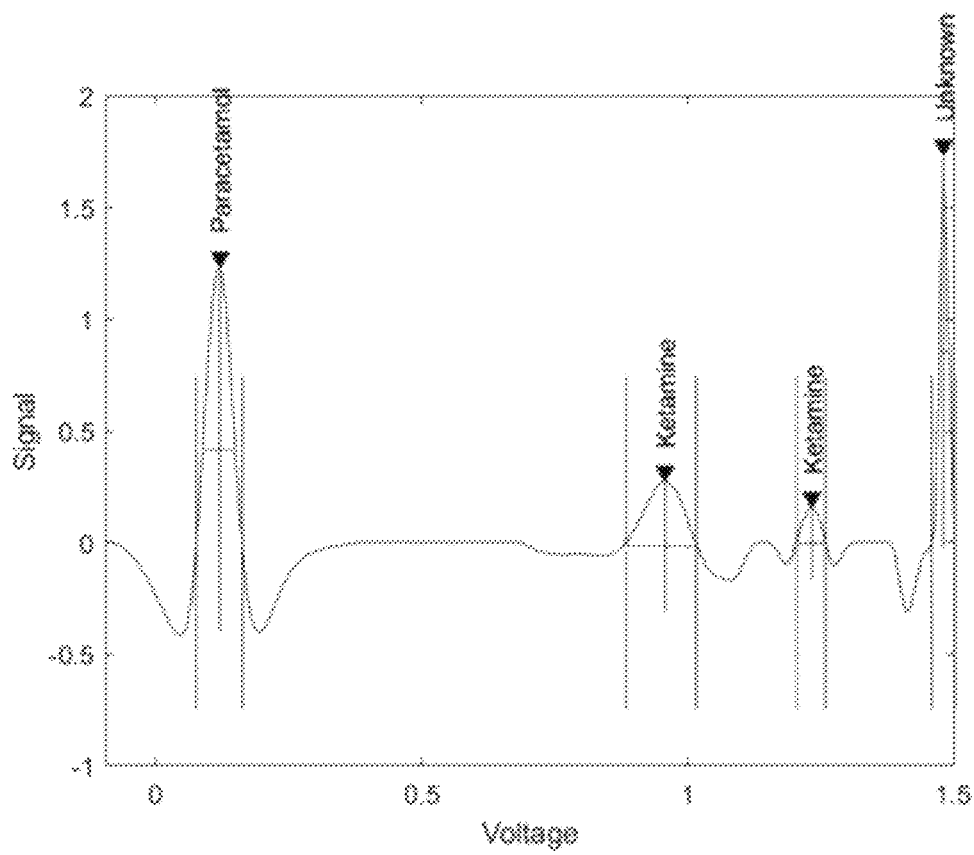
FIG. 4 shows an annotated electrochemical response in accordance with illustrative embodiments of the present invention.

Finally, the results were output by the computer program. This could be as a straightforward list of attributed analytes and/or visualized as in FIG. 4, showing the graph of FIG. 3 with two additional vertical lines marking each identified peak and a label displaying the analyte that was attributed to it.

Example 2

Figure 5:
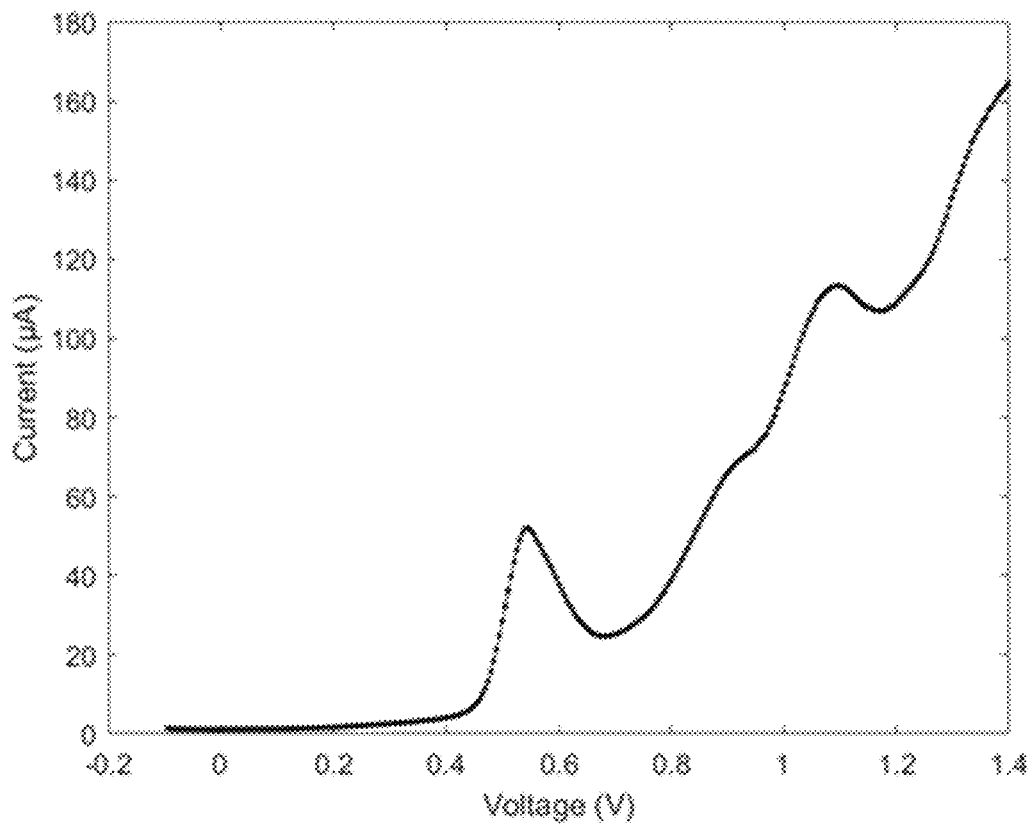
FIG. 5 shows a raw voltammogram in accordance with illustrative embodiments of the present invention.
Figure 6:
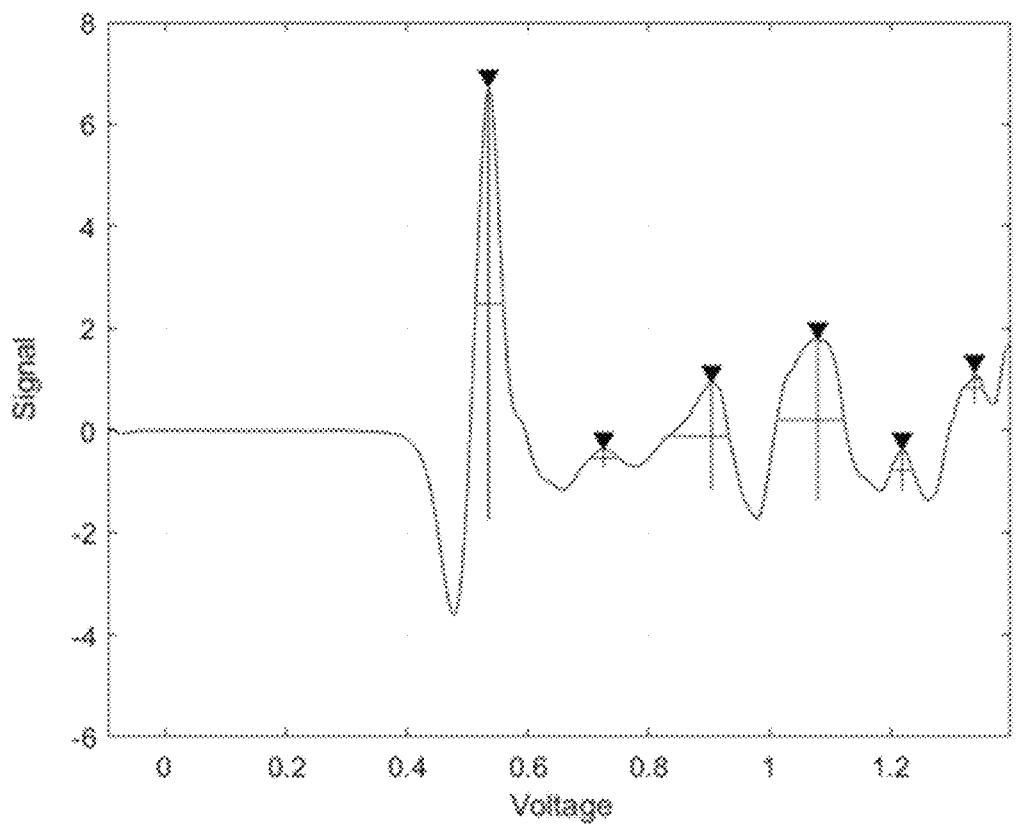
FIG. 6 shows a filtered electrochemical response in accordance with illustrative embodiments of the present invention.

Example 1 was repeated on several other electrochemical responses. FIG. 5 for instance illustrates a raw voltammogram of a different sample. Visualized in FIG. 6 is the outcome after baseline-correction of the raw voltammogram, applying a top-hat filter to the baseline-corrected voltammogram, identifying the peaks which exceed the predetermined height threshold and predetermined prominence threshold in the filtered electrochemical response, and determining the peak positions of these peaks. Next,— following a similar procedure as in Example 1, including the use of exception rules and unknown analytes—the computer program was able to attribute cocaine, caffeine, levamisole, phenacetin and lidocaine to the identified peaks and the results were output as both a list of these compounds and an annotated graph (not shown).

Figure 7:
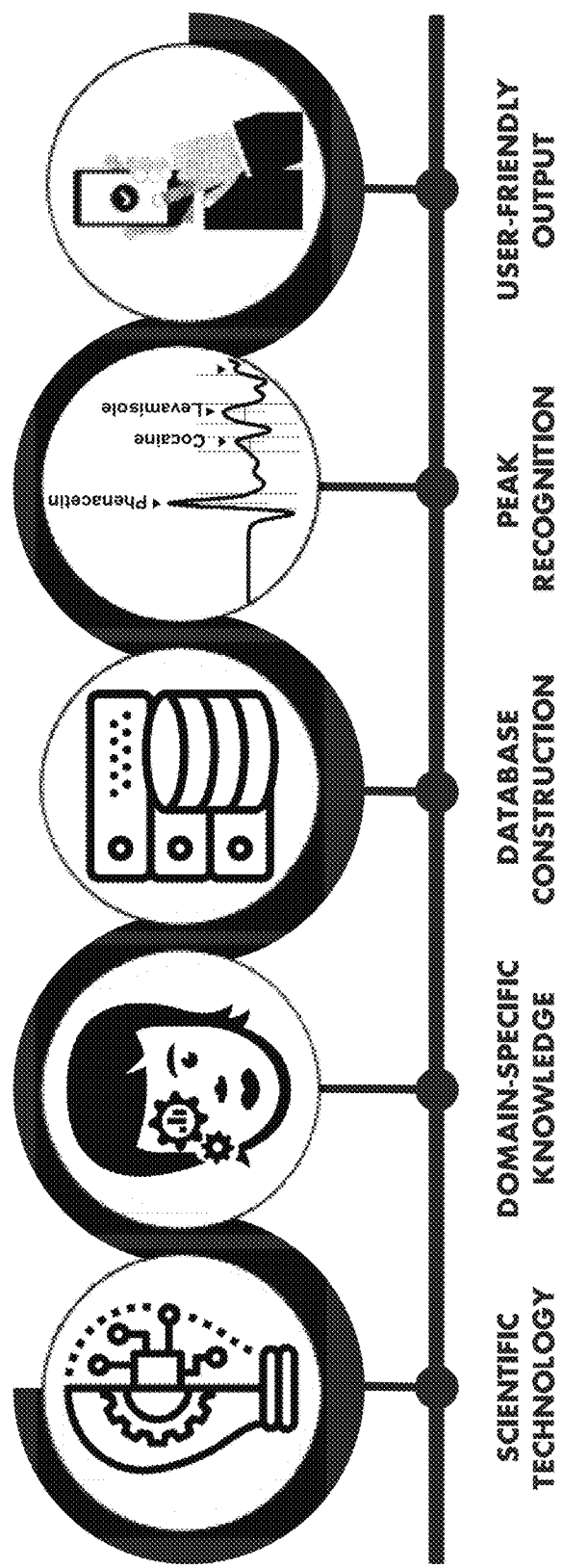
FIG. 7 shows a graphical abstract in accordance with illustrative embodiments of the present invention.

Example 3: Unlocking the Full Potential of Voltammetric Data Analysis: A Novel, Innovative Peak Recognition Algorithm Abstract (FIG. 7)

Bridging the gap between complex signal data output and clear interpretation by non-expert end-users is a major challenge many scientists face when converting their scientific technology into a real-life application. Currently, pattern recognition algorithms are the most frequently encountered signal data interpretation algorithms to close this gap, not in the least because of their straight-forward implementation via convenient software packages. Paradoxically, just because their implementation is so straight-forward, it becomes cumbersome to integrate the expert's domain-specific knowledge. In this work, a novel signal data interpretation algorithm is presented that uses this domain-specific knowledge as its fundament, thereby fully exploiting the unique expertise of the scientist. The new algorithm applies data preprocessing in an innovative way that transcends its usual purpose and is easy to translate into a software application. Ultimately, the novel algorithm offers a valuable tool for any researcher who wants to bring a scientific technology to society.

Introduction

Unraveling the valuable information hidden within complex data, and making that information understandable to non-experts, is a difficult task many scientists are confronted with when turning a scientific technology into a real-life application. Commonly, an expert in the research field is the only one capable of understanding and interpreting the complex data generated by a scientific device. However, if the complex output of the scientific device can be converted into a read-out comprehendible by non-experts, a major step is made towards the fulfillment of the point-of-need, paving the path for a successful application widely used.

Software is the ideal solution to bridge this gap between complex data output and non-expert, grace to its cost-, time- and labor efficiency. Furthermore, a software program can be integrated in the large majority of scientific devices. As such, a workflow can be created where an expert develops a software program and integrates it in the scientific device, after which any end-user can use the device without needing any scientific background. As a result, the group of potential users is drastically enlarged, and in extent the valuable time of the expert can be used elsewhere.

A suiting illustration of the aforementioned is given by the research field of electrochemical sensors, more specifically voltammetric sensors. Voltammetric techniques (e.g. linear sweep voltammetry (LSV), cyclic voltammetry (CV) and square wave voltammetry (SWV)) gain both qualitative and quantitative information of an analyte by applying a varying potential to the analyte and subsequently measuring the resulting current. The voltammetric readout, usually in the form of voltammograms (current vs potential plots), can thus be considered as being an extension to a classic amperometric readout which solely considers the current resulting from a single, fixed potential. The latter has found commercial applications (e.g. glucose sensor), while for voltammetric techniques this has proven more difficult due to the more complex readout. It demands years of research to acquire the expertise to extract valuable information (qualitative and/or quantitative) from these voltammograms. The development of an effective voltammetric detection method for the illegal drug cocaine is an excellent example of the aforementioned. It required many years of extensive research to come to a highly accurate (>98%), portable voltammetric cocaine sensor that outperforms the existing on-site identification tools. The suppressing and shifting nature of certain cutting agents (e.g. levamisole, benzocaine), in particular, made it challenging to develop an optimal strategy. The last major obstacle this voltammetric sensor has to overcome to become the ultimate tool law enforcement needs, is a translation of all the domain-specific knowledge that has been gathered over the years into a clear-cut interpretation thereof.

A commonly used approach to perform this translation, is the use of pattern recognition algorithms. These algorithms have elevated research in many domains such as image processing and computer vision to new heights and are rightfully praised. Voltammetry is no exception to this, and pattern recognition algorithms such as linear discriminant analysis (LDA), principal component analysis (PCA), soft independent modelling of class analogy (SIMCA) and more recently machine learning (ML), are frequently encountered. One reason pattern recognition methods have become such a success is the ease with which they are implemented.

Programming languages, such as Python or R, have highly convenient packages that allow a user to quickly run e.g. a PCA or construct and train a ML algorithm with limited prior knowledge. This is both a blessing and a curse, with the right expertise a user can quickly test different data analysis algorithms. However, the major risk occurs that the user no longer fully understands what happens between input and output, making the correct interpretation of the output cumbersome (so-called black box). The cohesion between the scientific technique that generates the data, and the data analysis method that interprets that data, is in danger of being lost. Especially, if it is also taken into account that the solutions these convenient software packages offer, are very general, precisely because they have to be so widely applicable. Incorporating domain-specific knowledge into them can therefore be anything but straight-forward, while it is precisely this knowledge that makes a scientific technology so valuable and powerful. Furthermore, the performance of pattern recognition algorithms, ML in particular, is strongly intertwined with the amount of available data. A lack thereof can result in poorly trained algorithms that are prone to overfitting and have bad generalizability, which is especially dangerous in combination with a black-box approach.

In this work, we propose a novel algorithm in which the domain-specific knowledge is the protagonist, rather than the algorithm itself. The expert's unique, subject-specific knowledge and the insight (s)he has in the data, is the starting point and the fundament on which the algorithm is build. The algorithm is developed for interpretation of voltammetric data, however it is envisioned that the scope of the algorithm can be extended to interpretation of signal data in other research fields. In voltammetry, the expert has generally excellent control over the different signals, i.e. (s)he can commonly authenticate the origin and presence of each signal. Therefore, instead of trying to unravel patterns in the data, the individual signals themselves will be used to extract information from the data. As such, it is assured that all the domain-specific knowledge of the expert is fully exploited, and in extent the risk of a black-box approach becomes non-existent. The bottleneck of this approach is thus the domain-specific knowledge, as opposed to e.g. the amount of available data to train an algorithm. This is far more desirable since a lack of domain-specific knowledge is a bottleneck for the scientific technology itself, and the data analysis algorithm as such does not create an additional bottleneck.

Results

Figure 8:
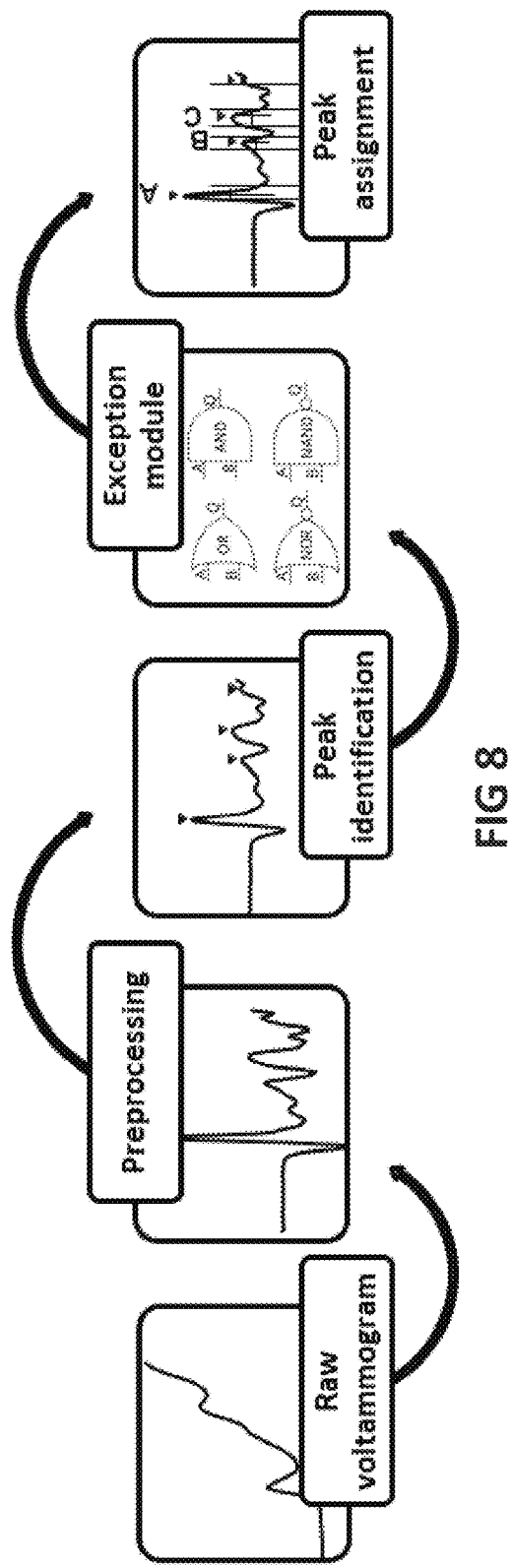
FIG. 8 schematically depicts an algorithm in accordance with illustrative embodiments of the present invention: in the depicted algorithm, a raw voltammogram is first modified with a baseline correction and a digital top hat filter to enrich the fingerprint and as such improve sensitivity. Then the relevant peaks are identified, and assigned to a compound using an internal database. An exception module can be introduced to incorporate additional rules prior to the peak assignment step.
Figure 9:
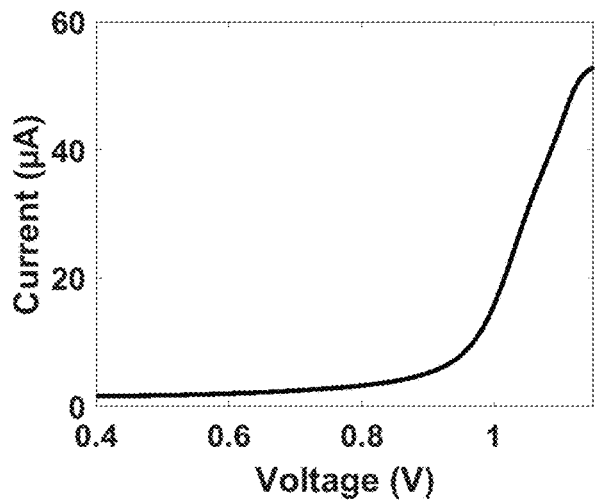
FIG. 9-FIG. 14 show the input (i.e. raw voltammogram; left) and output (i.e. annotated electrochemical response; right) for three case studies of the algorithm in accordance with illustrative embodiments of the present invention: (i) an illicit drug mixture of 50.0% MDMA and 50.0% 2-CB in phosphate buffer pH 5 (FIG. 9-FIG. 10), (ii) a 100.0% solution of the explosive 2,4,6-trinitrotoluene (TNT) in phosphate buffer pH 7 (FIG. 11-FIG. 12) and (iii) a drug street sample containing 31.0% cocaine, 2.8% phenacetin, 5.7% levamisole and an unknown percentage of mannitol analysed in phosphate buffer pH 12 buffer (FIG. 13-FIG. 14).
Figure 10:
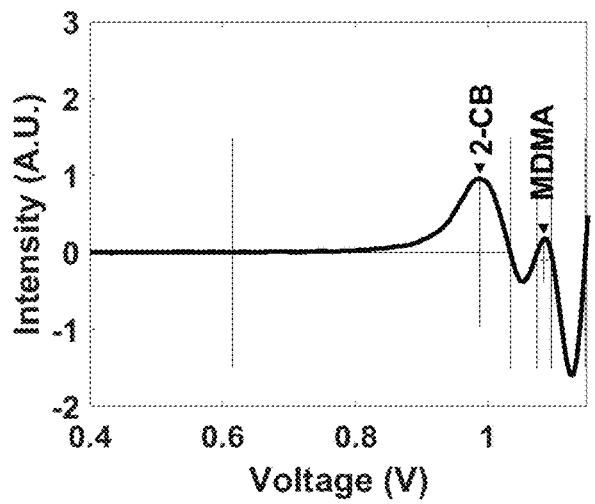
Figure 11:
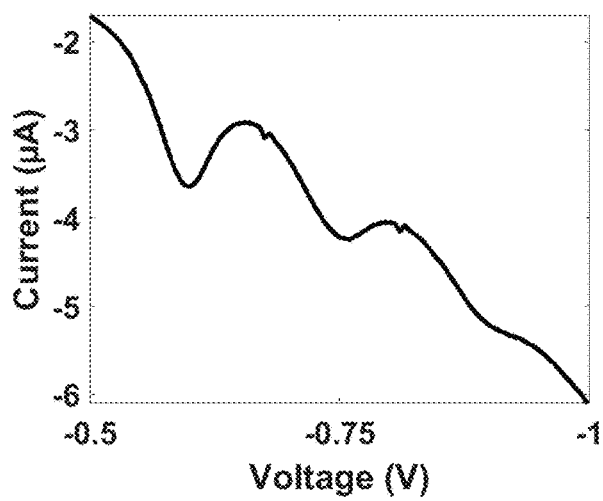
Figure 12:
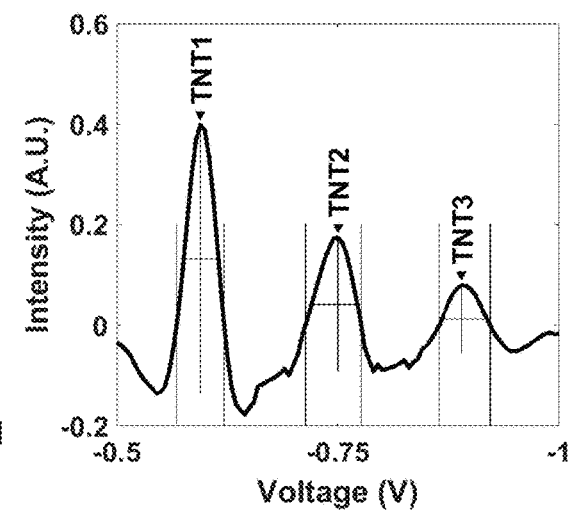
Figure 13:
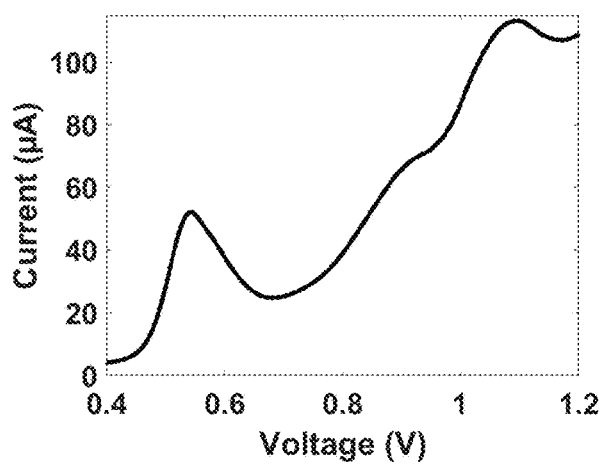
Figure 14:
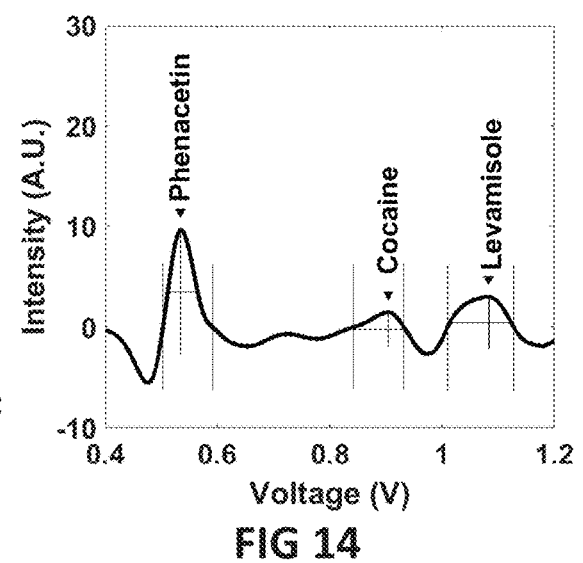

Algorithm overview. An innovative (voltammetric) signal data interpretation algorithm is developed which uses the locations of the individual peaks in a voltammogram to identify which compounds are present in a sample. FIG. 8 illustrates the different steps of the developed algorithm: initially a raw voltammogram is preprocessed to enrich the electrochemical fingerprint (i.e. the unique electrochemical signal or pattern specific for a certain analyte). After this preprocessing, the different peaks in the voltammogram are identified, followed by assignment of compounds to these peaks using an internal database. An exception module can be introduced in front of the peak assignment to include additional rules and requirements.

The algorithm utilizes individual peaks to assign the compounds present in the sample. It is therefore important to preprocess the raw voltammogram so that a voltammogram with distinct peaks is obtained. Preprocessing a raw signal to obtain a more easily interpretable signal is a common practice in signal processing. The novel algorithm will however demand a more innovative use of the preprocessing that transcends its usual purpose. Solely obtaining a more easily interpretable signal is not enough, all meaningful peaks should be brought to light, even those that might initially be hidden by e.g. a shoulder. In the following steps, these meaningful peaks will be selected for further processing based on peak height and prominence. It is thus crucial that all meaningful peaks are resolved and sufficiently separated, and a good preprocessing of the raw signal therefore plays a vital role in the success of the algorithm.

Initially, the baseline of the raw signal is corrected by using a moving average baseline correction, increasing peak distinction in the resulting voltammogram due to the removal of the background. However, overlapping peaks are not fully resolved by a baseline correction, limiting clear interpretation (cf. Supporting Information, Section S1). A more sophisticated preprocessing tool, a digital filter, is thus subsequently applied to further improve peak demarcation. The general purpose of a digital filter is to smooth the data through a convolution, thereby improving the precision of the data without distorting the signal tendency. Many different filters have been developed over time, often with great success, claiming a vital position in a wide variety of real-life applications. For this algorithm, a zero-area filter, more specifically a top hat filter, was selected. Besides their successful smoothing of the data, which is strived for here, zero-area filters have also proven to be beneficial for enhancing peak resolution. This improved resolution is particularly useful here, as the algorithm is based on the identification of individual peaks. The top hat filter is the zero-area filter of choice because of its low computing time, thereby keeping the algorithm optimally paced.

After enrichment of the raw voltammogram with a baseline correction and digital filter, the resulting peaks are evaluated on their relevance. In a further stage, compounds will be assigned to these peaks, and it is thus important to solely consider peaks that hold valuable information. Two parameters are introduced to define which peaks are interesting for further processing: (i) the minimum peak height and (ii) the minimum peak prominence. The prominence of a (signal) peak is a measure for how much the peak stands out relative to other peaks due to its intrinsic peak height and its peak location; it is akin to the concept of prominence in topography. A low isolated peak can be more prominent than one that is higher but is an otherwise unremarkable member of a tall range. In the context of interpreting a voltammetric response, less prominent peaks are those which largely overlap with other peaks and/or which do not stick out considerably from the background signal.

Once the relevant peaks are identified, a compound is assigned to each of these peaks by exploiting the expert's domain-specific knowledge on voltammetric analysis or fingerprint. The voltammetric fingerprint of a compound represents the unique relationship between that compound and its specific voltammetric response, thus containing extremely valuable information. Indeed, this relationship creates the perfect opportunity to link a (set of) voltammetric peak(s) to the presence of a specific compound. The algorithm takes full advantage of this opportunity by collecting all the voltammetric fingerprints into a database. The identified peaks are then one-by-one compared with the database, and a compound is assigned to a peak if a match is encountered.

The expert is the person par excellence to construct this database, as (s)he is the sole person who has the required domain-specific knowledge. The database is one of the greatest assets of the novel algorithm, as it offers a general approach to incorporate subject-specific knowledge.

Depending on the application, a further processing of the identified compounds can be included. In a detection sensor for example, an alarm or warning message could be associated with the detection of a specific compound to warn the end-user about its presence.

Illustration of the algorithm with three case studies. FIG. 9-FIG. 14 depicts three different applications of the developed software. In case study 1, the analysis of an illicit drug mixture of 50.0% methyleendioxymethamphetamine (MDMA) and 50.0% 2,5-dimethoxy-4-bromophenethylamine (2-CB) (both commonly found in the drug ecstasy) in phosphate buffer pH 5 is shown. The baseline correction successfully removed the background, after which the top hat filter revealed two peaks that were not visible at first. This example truly demonstrates the power of the preprocessing steps, unravelling the presence of two peaks that were invisible in the raw voltammogram. The two revealed peaks are eventually correctly identified using the internal database, and assigned the appropriate tags, i.e. MDMA and 2-CB.

In the second case study, a pure solution of the explosive 2,4,6-trinitrotoluene (TNT) in phosphate buffer pH 7 was analysed. Baseline removal and filtering led to a modified voltammogram with distinct peaks. The three characteristic reduction peaks of TNT were subsequently correctly identified and assigned the right tag after comparison with the corresponding database. Note that the intensities were inverted since the software searches for peak maxima instead of peak minima.

The third case study, a street sample of cocaine, illustrates that more complex samples are still correctly handled by the software. After analysis in phosphate buffer pH 12, the baseline correction and top hat filter converted yet again with success the raw voltammogram into a processed voltammogram without background and clear peak distinction. Cocaine was subsequently correctly assigned to the peak at 0.89 V, and in addition the cutting agents phenacetin and levamisole were correctly assigned as well. Note that the feature between the peak of phenacetin and the peak of cocaine did not pass the prominence threshold, and therefore was not selected for further processing. In FIG. 18-FIG. 22, all the different steps executed by the software are shown for case study 3 (cf. Supporting Information, Section S2).

The three case studies highlight the true power of the two data preprocessing steps. The preprocessing of voltammetry is a hot topic in voltammetry, involving the development and application of baseline removal algorithms and digital filters. The task of preprocessing the data is often unfairly limited to 'cleaning' the data (reducing noise and improving signal-to-noise ratio). Here, we have proven that preprocessing the data can handle more ambitious tasks. The moving average baseline correction in combination with the top hat filter are the ideal tandem to reveal hidden features, improve peak demarcation and as such improve sensitivity. The resulting enriched voltammogram after preprocessing can thus be an objective in itself. An expert might come to new insights as new features that were masked in the initial voltammogram are revealed in the enriched voltammogram.

Figure 15:
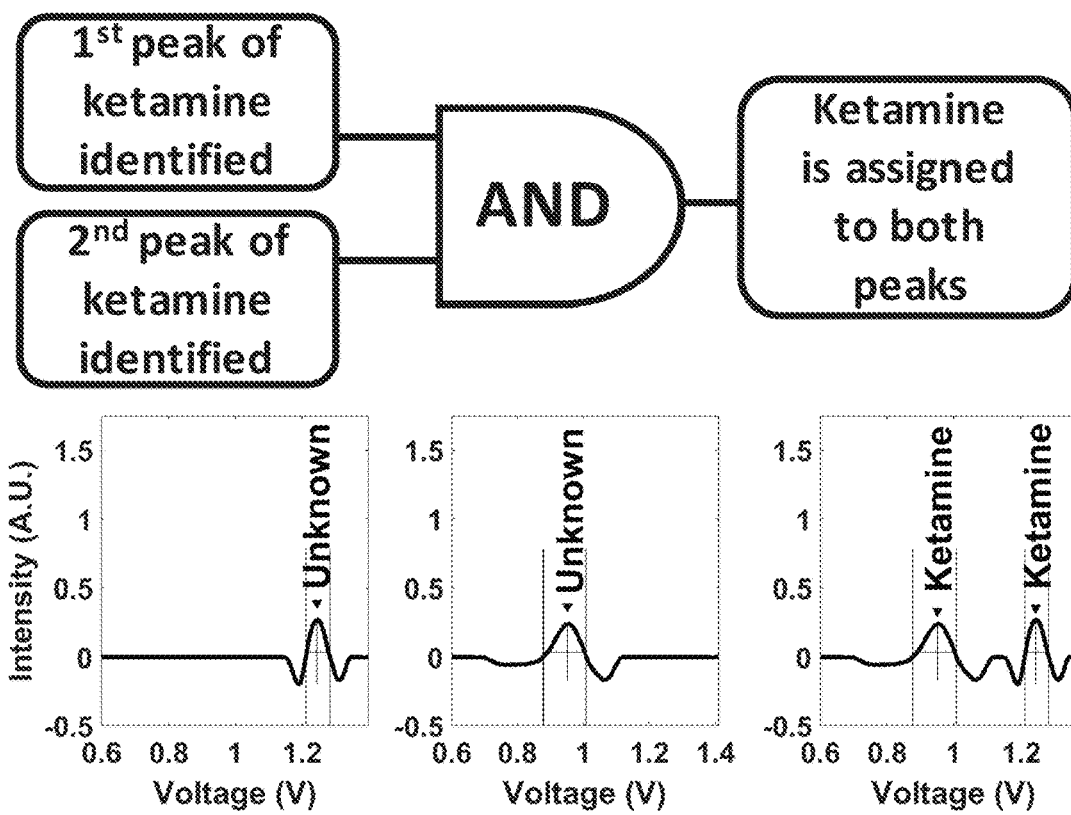
FIG. 15-FIG. 16 schematically depicts the incorporation of additional rules via an exception module in accordance with illustrative embodiments of the present invention.
Figure 16:
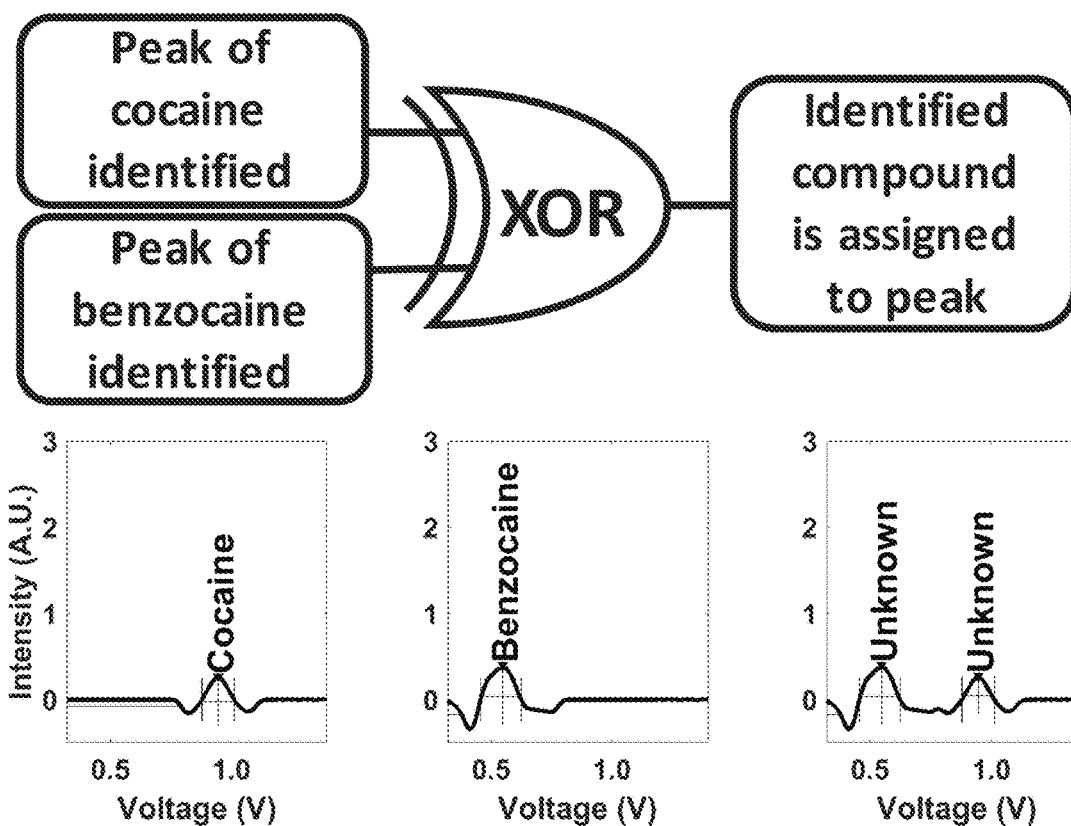

Special cases. In each of the case studies presented in FIG. 9-FIG. 14, each peak could easily be assigned to a single compound. This 1-on-1 assignment will be sufficient in most of the cases where this software is applied. However, some applications require additional rules. The algorithm facilitates the incorporation of such additional rules through an exception module that is placed right in front of the compound assignment (FIG. 15-FIG. 16). This exception module is the perfect tool to bring domain-specific knowledge into the algorithm in a straight-forward manner. A parallel with the concept of logic gates is made to illustrate what an additional rule looks like. However, the additional rules that can be incorporated are not limited to this concept (cf. Supporting Information, Section S3).

FIG. 15 illustrates how the presence of two (or more) characteristic peaks of a compound can be required when assigning a compound. An example is the voltammogram of the illicit drug ketamine in phosphate buffer pH 12. This compound showcases two characteristic peaks, located at 0.90 V and 1.25 V respectively, and it can thus be required that both peaks need to be identified before ketamine is assigned to the voltammogram. The identification of only one of the peaks is thus not sufficient for assignment. Considering the TNT case study in FIG. 11-FIG. 12, the aforementioned thus allows to incorporate an exception module that requires the presence of all three TNT peaks prior to assignment.

Another possible exception is an additional rule that prevents two compounds from being assigned together (FIG. 16). Such an additional rule can be of great use when one of two compounds is known to cause a shift of the other one's signal. In that case it is a good safety measure to avoid their mutual assignment to prevent assignment errors. The implementation of this additional rule can be compared to an exclusive OR-gate, i.e. a true output is only given in case of an odd number of true inputs. In the example shown in FIG. 16, cocaine has one signal (0.82 V), as has the cutting agent benzocaine (0.41 V). Benzocaine is known to cause a shift of the signal of cocaine, and an additional rule is thus incorporated. If both aforementioned signals (0.41 V and 0.82 V) are encountered together, cocaine and benzocaine will not be assigned to these peaks.

Discussion

In this work we have introduced a novel algorithm for the interpretation of voltammetric signal data. Instead of relying on the extraction and interpretation of complex patterns in the data, the interpretation is executed directly by comparing the individual peaks with an internal database. This database is constructed using the expert's domain-specific knowledge, thereby fully utilizing this unique expertise.

Before comparison with the database, two preprocessing steps, a baseline correction and a digital filter, are applied to the signal to remove the background and improve peak demarcation. This preprocessing tandem greatly enriches the voltammetric signal, revealing peaks that were visually hidden in the raw signal. These peaks are later on used for compound assignment and the preprocessing tandem consequently claims a key role in the algorithm. The increased sensitivity thus obtained is therefore of great importance in this algorithm, but can equally well be of exceptional value for any researcher seeking to extract hidden information from signal data.

Two parameters, minimum peak height and minimum peak prominence, are introduced to select the relevant peaks for further processing. A good parameter value choice is necessary to ensure that only those peaks are selected that hold valuable information. Values that are too lenient will result in a large pool of peaks that will further be processed, some of which might solely originate from noise.

Eventually, the selected peaks are compared with the internal database and assigned a compound if a match is encountered. The complexity of the database depends on the application and the amount of different compounds that need to be identified. The database of a detection sensor which targets a single compound could consist of that sole compound itself, whereas the database of an identification tool for e.g. waste water analysis might consist of a large list of compounds. Additional rules, to e.g. build in restrictions or exceptions, can be included in the algorithm via an exception module. The database and exception module enable a very user-friendly integration of subject-specific knowledge into the algorithm, thereby providing quick access to tailor-made solutions.

Furthermore, the algorithm is designed in such a way that a single expert can optimize the algorithm (choose peak identification parameter values, build database, . . . ), translate it into a suitable software program and integrate the latter in a scientific device. Ideally, a non-expert can then use the device without prior knowledge of voltammetry or even science. The expert is only involved in the setup and integration, which frees up time to perform more analyses.

Even though the algorithm was developed for interpretation of voltammetric signal data, it is envisioned that the scope can transcend the field of voltammetry and be applied in other fields of science that handle signal data.

Methods

Voltammetric measurements. Electrochemical measurements, more specifically square wave voltammetric analyses, were carried out using a PalmSens4 potentiostat with PSTrace 5.7 software (Utrecht, The Netherlands). Disposable carbon ItalSens IS-C Screen Printed Electrodes (SPE) were purchased from PalmSens (Utrecht, The Netherlands) and were used during all electrochemical measurements. The SPE's contain an internal silver pseudo reference electrode and a carbon counter electrode. All experiments were performed by applying 50 µL of solution onto the SPE. All SWV measurements were carried out with a step potential of 5 mV, amplitude of 25 mV and frequency of 10 Hz. The following buffers were used during the electrochemical measurements: 0.1M phosphate buffer pH5, 0.1M phosphate buffer pH 7 and 0.1M phosphate buffer pH 12. The measurement of the MDMA/2-CB mixture (FIG. 4—example 1) was preceded by a pretreatment (−0.8V/300 s). The measurement of TNT (FIG. 4—example 2) was preceded by a 10 minute argon purge of the SPE cell to remove the influence of oxygen.

Data processing. The moving average baseline correction was applied using the function integrated in the PSTrace 5.7 software. All other processing of the data was performed with Matlab R2018a (MathWorks, Natick, MA, USA) software, including its Signal Processing Toolbox™.

Moving average baseline correction. The first step in the software framework is the removal of the baseline using a moving average baseline correction. The raw voltammogram is used as an input. For every two data points, the average current value is calculated, thereby reducing the amount of data points by a factor two. Every resulting data point $A_i$ is subsequently compared to the average $A'_i$ of the neighboring points $A_{i-1}$ and $A_{i+1}$. Then it is checked if $A_i$ is larger than $A'_i$ (for oxidation peaks). If this is the case, $A_i$ is replaced by $A'_i$. This is repeated until no more replacements take place or until the iteration threshold of 1000 is reached. Eventually, the number of data points is extrapolated to the original number. The resulting data points represent the increasing background and are thus subtracted from the raw voltammogram. The resulting voltammogram contains more visible oxidation peaks and is thus more easily interpretable.

Top hat filter. The top-hat filter is a so-called zero-area filter that has a central window with an odd number of channels w and two side windows each v channels wide. The value of the filter coefficients (k and $h_k$) follows from the zero-area constraint:

$$h_k = \begin{cases} -\frac{1}{2v}, & -v-\frac{w}{2} \leq k < -\frac{w}{2} \\ \frac{1}{w}, & -\frac{w}{2} \leq k \leq +\frac{w}{2} \\ -\frac{1}{2v}, & +\frac{w}{2} < k \leq \frac{w}{2}+v \end{cases}$$

The filtered (i.e. transformed) electrochemical response $y^*_i$ is then obtained by the convolution of the electrochemical response with the filter:

$$y^*_i = \sum_{k=-v-w/2}^{v+w/2} h_k y_{i+k}.$$

Peak identification. Two parameters are defined to identify the peaks: the minimum peak height and the minimum peak prominence. The first one speaks for itself, whereas the second one might require some more explanation. A marker is placed on the top of a potential peak. Subsequently, a horizontal line is drawn through this marker until (i) it crosses the signal because it encounters a higher peak or (ii) it reaches the left or right end of the signal. Then, the minimum of the signal in each of the two intervals defined in the previous step is searched. This point is either a valley or one of the signal endpoints. The higher of the two interval minima specifies the reference level. The height of the peak above this level is its prominence. Each peak that has a value higher than the defined minimum peak height and minimum peak prominence is identified as a peak that will be processed further throughout the algorithm.

Reagents & Solutions. d,l-methyleendioxymethamphetamine·HCl (d,l-MDMA·HCl) standard was purchased from Lipomed (Arlesheim, Switzerland). A 2,4,6-trinitrotoluene (TNT) sample was provided by the Dutch Forensic Institute (NFI, The Hague, The Netherlands). 2,5-dimethoxy-4-bromophenethylamine (2-CB) and the cocaine street sample were obtained from the National Institute for Criminalistics and Criminology (Brussels, Belgium). Analytical grade salts of potassium chloride and potassium phosphate, as well as potassium hydroxide, were purchased from Sigma-Aldrich (Overijse, Belgium). All solutions were prepared in 18.2 MΩ cm-1 doubly deionized water (Milli-Q water systems, Merck Millipore). The pH was measured using a CyberScan 510 pH-meter from Eutech Instruments (Landsmeer, The Netherlands) connected to a HI1131 glass bodied pH electrode from Hanna Instruments (Bedfordshire, United Kingdom). Adjustment of the pH was performed using a 100 mM KOH solution.

Supporting Information:

Section S1: Illustration of the preprocessing steps. The algorithm employs two different preprocessing steps, baseline correction and digital filter, to improve peak demarcation. The objective of the preprocessing is to reveal all meaningful signals, and prepare them for further processing in the algorithm. In FIG. 17, the effect of the baseline correction and filter on a raw voltammogram is illustrated. The baseline correction removes the background, however not all signals are fully resolved. Between 0.8V-1.1V a shoulder is still visible, and an additional preprocessing step is thus required. A digital filter, here the top hat filter, is employed to reach this objective. Indeed, after employing the filter, the shoulder is resolved in two distinct peaks.

Ultimately, the voltammetric fingerprint is thus greatly enriched by the preprocessing steps.

Section S2: Detailed illustration of the peak recognition algorithm using an example. Hereafter the different steps of the peak recognition algorithm are illustrated using case study 3 from FIG. 13-FIG. 14. The sample is analyzed in phosphate buffer pH 12 (FIG. 18), the composition is as follows: 31% cocaine, 2.8% phenacetin, 5.7% levamisole and an unknown percentage of mannitol. First the baseline is corrected using the moving average baseline algorithm (FIG. 19). Then a top hat filter is applied to improve peak demarcation (FIG. 20). Subsequently the peaks are identified (FIG. 21), after which eventually the compounds are assigned to the right peaks by comparison with an internal database (FIG. 22).

Section S3: Illustration of additional rules in exception module. In the exception module, different additional rules can be integrated. The following list illustrates a variety of additional rules:

Priority rules:
  If compound A and compound B occur in a similar region in the voltammogram, the identification of compound A can be prioritized over the identification of compound B. This is useful e.g. if compound A is encountered more frequently than compound B.
  Where one or more compounds are known to frequently occur together and all the signals of these compounds have been identified, then prioritize the assignment of these compounds.
Multiple peaks rule: For a compound with a fingerprint with multiple signals, it can be required that all (or a selection of) signals need to be identified prior to assignment.
Shift rule: Where the presence of a compound is known to shift the peak of one or more other compounds and the former has been associated, use alternative predetermined database entry for the latter and alter the association accordingly.
Stop rule: Stop the algorithm if a signal in a certain region is encountered.

It is to be understood that although preferred embodiments, specific constructions and configurations, as well as materials, have been discussed herein for devices according to the present invention, various changes or modifications in form and detail may be made without departing from the scope and technical teachings of this invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A computer-implemented method for interpreting an electrochemical response, comprising the steps of:
   a) providing an electrochemical response which is baseline-corrected;
   b) identifying in the electrochemical response one or more peaks which exceed a predetermined height threshold and a predetermined prominence threshold, each identified peak having a peak position;
   c) providing a predetermined peak position range for each of a plurality of analytes; and
   d) attributing one or more of the analytes to the peaks identified in step b, by, for each peak, associating the peak with an analyte when the peak position falls within the predetermined peak position range for said analyte.

2. The computer-implemented method according to claim 1, wherein step a comprises:
   a1) providing an electrochemical response, and
   a2) performing a baseline-correction on the electrochemical response.

3. The computer-implemented method according to claim 1, wherein the electrochemical response is baseline-corrected using a moving average baseline-correction.

4. The computer-implemented method according to claim 1, further comprising a step a'—before step b—of:
   a') applying a filter to the electrochemical response so as to improve peak demarcation.

5. The computer-implemented method according to claim 4, wherein the filter is a zero-area rectangular filter.

6. The computer-implemented method according to claim 4, wherein step a' is performed after or concurrently with step a.

7. The computer-implemented method according to claim 1, wherein step d further comprises altering the association of the peak with one or more of the analytes based on a predetermined exception rule.

8. The computer-implemented method according to claim 7, wherein altering the association of the peak with one or more of the analytes comprises:
   disassociating the peak from one or more of the analytes, and/or
   associating the peak with one or more of the analytes.

9. The computer-implemented method according to claim 1, further comprising a step e—after step d—of:
   e) outputting the attributed analytes.

10. The computer-implemented method according to claim 1, wherein the plurality of analytes comprises one or more from the list of drugs, adulterants, antibiotics and explosives.

11. A computer-implemented method for detecting one or more analytes in a sample, comprising the steps of:
   providing an electrochemical response of the sample, and
   performing the method according to claim 1 using said electrochemical response of the sample.

12. The computer-implemented method according to claim 11, wherein providing an electrochemical response of the sample comprises performing an electrochemical measurement on a solution comprising the sample.

13. A data processing system adapted to carry out the computer-implemented method according to claim 1.

14. A computer program comprising instructions which, when the program is executed by a computer, cause the computer to carry out the computer-implemented method according to claim 1.

15. A computer-readable medium comprising instructions which, when executed by a computer, cause the computer to carry out the computer-implemented method according to claim 1.

* * * * *